(12) United States Patent
Türkyilmaz et al.

(10) Patent No.: US 10,130,618 B2
(45) Date of Patent: Nov. 20, 2018

(54) PHARMACEUTICAL COMBINATIONS OF DABIGATRAN AND PROTON PUMP INHIBITORS

(71) Applicant: SANOVEL ILAC SANAYI VE TICARET ANONIM SIRKETI, Istanbul (TR)

(72) Inventors: Ali Türkyilmaz, Istanbul (TR); Mehtap Saydam, Istanbul (TR); Yildiz Gülkok, Istanbul (TR); Nur Kirat Uzunogullari, Istanbul (TR); Sevgi Gökcek, Istanbul (TR)

(73) Assignee: SANOVEL ILAC SANAYI VE TICARET ANONIM SIRKETI, Istanbul (TR)

( * ) Notice: Subject to any disclaimer, the term of this patent is extended or adjusted under 35 U.S.C. 154(b) by 0 days.

(21) Appl. No.: 15/303,176

(22) PCT Filed: Apr. 9, 2015

(86) PCT No.: PCT/EP2015/057702
§ 371 (c)(1),
(2) Date: Oct. 10, 2016

(87) PCT Pub. No.: WO2015/155281
PCT Pub. Date: Oct. 15, 2015

(65) Prior Publication Data
US 2017/0035745 A1 Feb. 9, 2017

(30) Foreign Application Priority Data
Apr. 11, 2014 (TR) .................................. 2014/04232

(51) Int. Cl.
*A61K 31/4439* (2006.01)
*A61K 9/16* (2006.01)
*A61K 9/50* (2006.01)
*A61K 9/20* (2006.01)
*A61K 31/5377* (2006.01)

(52) U.S. Cl.
CPC ........ *A61K 31/4439* (2013.01); *A61K 9/1635* (2013.01); *A61K 9/1652* (2013.01); *A61K 9/1676* (2013.01); *A61K 9/2077* (2013.01); *A61K 9/2081* (2013.01); *A61K 9/5084* (2013.01); *A61K 31/5377* (2013.01)

(58) Field of Classification Search
None
See application file for complete search history.

(56) References Cited

U.S. PATENT DOCUMENTS

| | | | |
|---|---|---|---|
| 3,536,809 A | 10/1970 | Applezweig | |
| 3,845,770 A | 11/1974 | Theeuwes et al. | |
| 3,916,899 A | 11/1975 | Theeuwes et al. | |
| 4,853,230 A | 8/1989 | Lovgren et al. | |
| 2003/0181488 A1 * | 9/2003 | Brauns | A61K 31/4439 514/338 |
| 2004/0077869 A1 | 4/2004 | Reddy et al. | |
| 2006/0204585 A1 * | 9/2006 | Hall | A61K 9/0056 424/489 |
| 2006/0247278 A1 * | 11/2006 | Sieger | C07D 401/12 514/338 |

FOREIGN PATENT DOCUMENTS

| | | | |
|---|---|---|---|
| EP | 1129088 | 5/2001 | |
| EP | 1870100 | 3/2003 | |
| EP | 1877395 | 1/2008 | |
| EP | 2722033 A1 * | 4/2014 | ........ A61K 31/4439 |
| EP | 2722033 A1 * | 4/2014 | ........ A61K 31/4439 |
| WO | WO 94/27988 | 12/1994 | |
| WO | WO 96/24338 | 8/1996 | |
| WO | WO 98/37075 | 8/1998 | |
| WO | WO 00/78745 A2 | 12/2000 | |
| WO | WO 2006/114415 A2 | 11/2006 | |
| WO | WO 2012/077136 | 6/2012 | |

OTHER PUBLICATIONS

Agewall et al., "Expert position paper on the use of proton pump inhibitors in patients with cardiovascular disease and antithromiotic therapy", Eur Heart J 34: 1708-1717 (2013).*
Huisman et al., Thromb Haemost 107:838 (2012) (Year: 2012).*
Hankey et al., Circulation 123: 1436 (2011) (Year: 2011).*
Okada et al., "Exfoliative esophagitis and esophageal ulcer induced by dabigatran", Endoscopy 44: E23-E24 (2012) (Year: 2012).*
Strand et al. "25 Years of proton pump inhibitors: a comprehensive review", Gut and Liver 11: 27-37 (2017) (Year: 2017).*
Yamashita et al., "Observational study of the effects of dabigatran on gastrointestinal symptoms in patients with non-valvular atrial fibrillation", J Arrhythmia 30: 478 (2014) (Year: 2014).*
Agewall et al., "Expert position paper on the use of proton pump inhibitors in patients with cardiovascular disease and antithrombotic therapy", Eur Heart J 34: 1708-1717 (2013) (Year: 2013).*
Agewall et al., "Expert position paper on the use of proton pump inhibitors in patients with cardiovascular disease and antithrombotic therapy," *European Heart Journal*, 34:1708-1715, 2013.

(Continued)

*Primary Examiner* — Thor Nielsen
(74) *Attorney, Agent, or Firm* — Kilpatrick Townsend & Stockton LLP

(57) ABSTRACT

This invention is a novel pharmaceutical composition comprising dabigatran or a pharmaceutically acceptable salt thereof in combination with a proton pump inhibitor for use in the antithrombotic treatment with preventing or reducing the risk of a gastrointestinal disorder.

24 Claims, 8 Drawing Sheets

(56) References Cited

OTHER PUBLICATIONS

Figure 1:
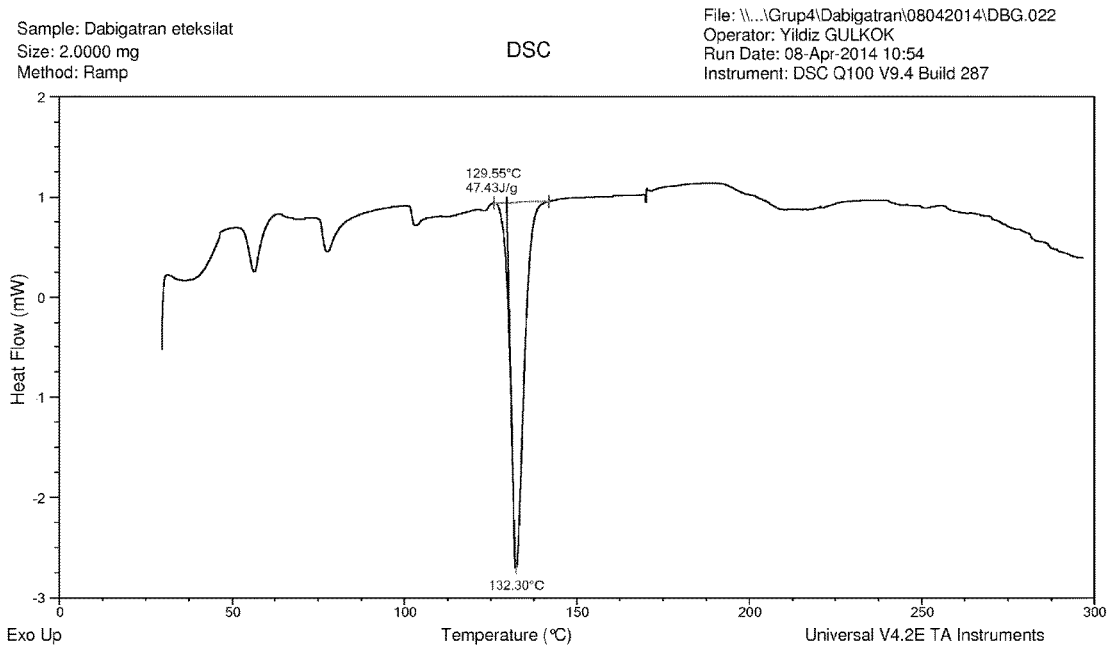

Niranjan Kottala et al., Evaluation of the Performance Characteristics of Bilayer Tablets: Parts I. Impact of Material Properties and Process Parameters on the Strength of Bilayer Tablets, *AAPS Pharmscitech*, Springer New York LLC, 13:4:1236-1242, 2012.
International Search Report for International Appl. No. PCT/EP2015/057702, Int'l Filing Date Apr. 9, 2015.
Abstract machine English language translation EP 1870100 A1.

* cited by examiner

PHARMACEUTICAL COMBINATIONS OF DABIGATRAN AND PROTON PUMP INHIBITORS

CROSS REFERENCE TO RELATED APPLICATIONS

This application is a U.S. national phase application of international application, PCT/EP2015/057702, filed Apr. 9, 2015 which claims the priority of Turkish application No. TR 2014/04232, filed Apr. 11, 2014, the disclosure of which is incorporated by reference herein.

FIELD OF INVENTION

This invention is a novel pharmaceutical composition comprising dabigatran or a pharmaceutically acceptable salt in a combination with a proton pump inhibitor and at least one pharmaceutically acceptable excipient.

More specifically, this invention relates to pharmaceutical composition comprising dabigatran or a pharmaceutically acceptable salt thereof in combination with a proton pump inhibitor for use in the antithrombotic treatment with preventing or reducing the risk of a gastrointestinal disorder administrated by oral, parenteral, intramuscular or topical route.

BACKGROUND OF INVENTION

Thrombotic disorders are characterized by formation of a thrombus that obstructs vascular blood flow locally or detaches and embolizes to occlude blood flow downstream. Thrombotic disorders are a major cause of death in the industrialized world.

Presently there are numerous antithrombotic drugs which are widely available, they also called as Direct Thrombin Inhibitors (DTIs) which are a class of medication that act as anticoagulants (delaying blood clotting) by directly inhibiting the enzyme thrombin. In another exemplary embodiment, the DTI is univalent. In another exemplary embodiment, the DTI is bivalent. In an exemplary embodiment, the DTI is a member selected from hirudin, bivalirudin (IV), lepirudin, desirudin, argatroban (IV), dabigatran, dabigatran etexilate (oral formulation), melagatran, ximelagatran (oral formulation but liver complications) and prodrugs thereof.

Dabigatran etexilate (Formula I), which is already known from WO 98/37075, is a direct thrombin inhibitor indicated to reduce the risk of stroke and systemic embolism in patients with non-vascular atrial fibrilitaion.

Formula I

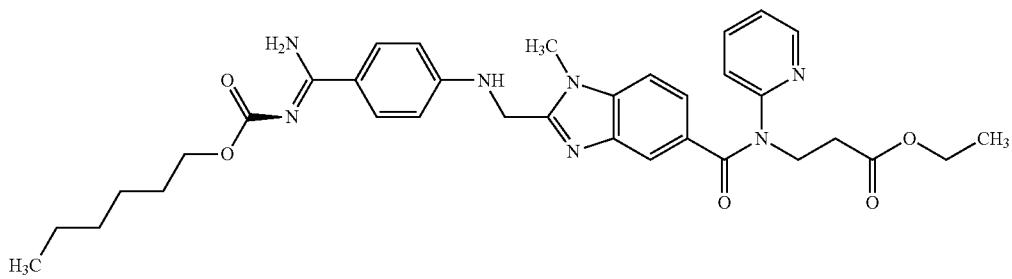

Dabigatran etexilate

The methane sulphonic acid addition salt of dabigatran etexilate, which is commercially available under the trade name PRADAXA®, is disclosed in EP1870100, also disclosed, pellet composition of dabigatran etexilate mesylate (Formula II). This composition is formulated with a core material consisting of organic acid and an active layer which encloses the core.

Formula II

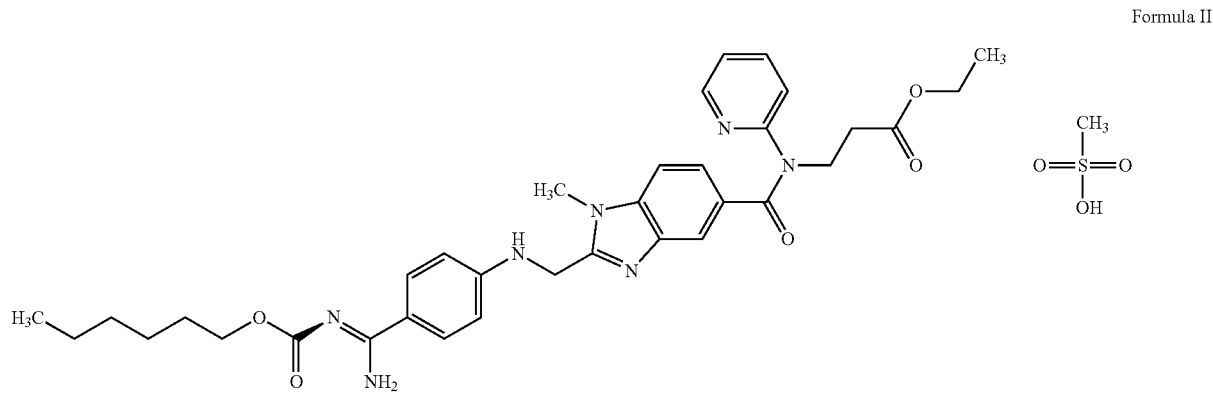

Dabigatran etexilate mesylate

Apart from the mesylate salt of dabigatran etexilate, other acid addition salts of the compound are provided in prior art. For example, WO2012/077136 is directed to the oxalate salt of dabigatran etexilate and besides, its hydrochloride salt is identified in EP1877395. These various form of dabigatran etexilate are prepared to facilitate the development of pharmaceutical composition. An active agent should meet some physicochemical requirements in order to be capable of being used in pharmaceutical compositions. These requirements considerably depend on the physicochemical properties of the active agent used in pharmaceutical composition.

However, dabigatran etexilate is associated with side effects. The administration of antithrombotic agents, such as dabigatran etexilate, have been associated with gastrointestinal disorders such as ulcers and gastrointestinal bleeding. In addition, the administration of dabigatran etexilate, may make some patients more susceptible to the ulcerogenic effects of ulcerogenic stimuli. It appears that a major factor contributing to the development of these gastrointestinal disorders is the presence of acid in the stomach and upper small intestine. While the mechanisms associated with ulcers and gastrointestinal bleeding are not entirely known, there are many causes of ulcers, including stress, alcohol irritation, Helicobacter pylori infection, and the side effects of non-steroid anti-inflammatory drugs. Patients in need of long term antithrombotic drug therapy often may interrupt or not receive such therapy due to gastrointestinal disorders, and as a result, patients are deprived of beneficial antithrombotic drug therapy. There is a need for oral pharmaceutical combination formulations to reduce or eliminate the gastrointestinal disorders associated with use of antithrombotic drugs.

Proton pump inhibitors (PPI) are acid labile compounds useful for inhibiting gastric acid secretion. The problems arisen from this acid labile characteristic of these compounds is overcome by providing a formulation that dissolves in the intestines rather than the acidic environment of the stomach.

Using an antacid or an alkaline excipient with a PPI in the formulation is one method used in the art to reduce the acidity of the gastrointestinal environment. Another one is to provide an enteric coating for the composition comprising the acid labile PPI.

It is known in the state of art that the enteric polymers with acidic nature are not compatible with the proton pump inhibitors and the alkaline excipients used in the formulation. To overcome this problem an inert intermediate layer may be introduced, such as in the prior art. In U.S. Pat. No. 4,853,230 and WO 96/24338 enteric coated formulations with an alkaline active ingredient containing core and a separating layer are described.

Another role of the enteric coating is to provide a modified release. The delivery of the active ingredient to specific sites in the gastrointestinal tract is achieved by enteric coatings. These polymers can also prolong or extend the amount of active ingredient released from the dosage form.

Lansoprazole is a proton pump inhibitor (PPI) which inhibits the stomach's production of gastric acids. Lansoprazole is a racemate 1:1-mixture of the enantiomers dexlansoprazole and levolansoprazole. Dexlansoprazole is an enantiomerically pure active ingredient of a commercial drug as a result of the enantiomeric shift.

In prior art, there are many patents including benzimidazoles such as lansoprazole and its R-enantiomer, dexlansoprazole in several different pharmaceutical compositions. Crystal form of R-lansoprazole is described in EP1129088.

One of the active ingredient from the group of PPI, dexlansoprazole is the R-enantiomer of lansoprazole which inhibits gastric acid secretion (a proton pump inhibitor). Its chemical name is (+)-2-[(R)-{[3-methyl-4-(2,2,2-trifluoroethoxy)pyridin-2-yl]methyl} sulfinyl]-1H-benzimidazole and its chemical structure is shown in the Formula III.

Formula III

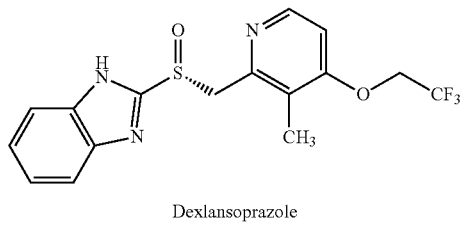

Dexlansoprazole

Delayed release capsule form of dexlansoprazole is in the market and it is administered orally in a therapeutic dose of 30 mg and 60 mg.

As other benzimidazole compounds, dexlansoprazole has also poor stability and is unstable to acidic medium, humidity, light and sensitive to heating. When orally administrated, it may not be able to sufficient activity since it is decomposed by gastric acid and the like. Thus, several problems occur in formulating such compound into oral pharmaceutical dosage forms because of the acidic environmental of the stomach. In particular, it will be rapidly decomposed and change colour under moist conditions or in acidic to neutral aqueous solution.

Another one from the group of PPI is the compound 5-methoxy-2-[[(4-methoxy-3,5-dimethyl-2-pyridinyl) methyl]sulfinyl]-1H-benz imidazole, having the generic name omeprazole, and therapeutically acceptable alkaline salts thereof are described in U.S. Pat. No. 4,255,431 to Junggren et al., EP 5129 and EP 124 495, respectively. Omeprazole and structurally similar sulfoxide compounds are known inhibitors of gastric acid secretion and are used as anti-ulcer agents. The sulfur atom of the sulfoxide group in asymmetrically substituted sulfoxides is chiral. Therefore, omeprazole and related sulfoxides exhibit optical isomerism at the sulfur atom of the sulfoxide. In fact, omeprazole exists as a pair of enantiomers; the S (−) enantiomer is referred to as esomeprazole.

Esomeprazole is a proton pump inhibitor that suppresses gastric acid secretion by specific inhibition of the H+/K+-ATPase in the gastric parietal cell. The S- and R-isomers of omeprazole are protonated and converted in the acidic compartment of the parietal cell forming the active inhibitor, the achiral sulphonamide. By acting specifically on the proton pump, esomeprazole blocks the final step in acid production, thus reducing gastric acidity. This effect is dose-related up to a daily dose of 20 to 40 mg and leads to inhibition of gastric acid secretion. Its chemical name is (S)-5-methoxy-2-[(4-methoxy-3,5-dimethylpyridin-2-yl) methylsulfinyl]-3H-benzoimidazole and its chemical structure is shown in the Formula IV. Certain salts of single enantiomers of omeprazole and their preparation are disclosed in WO 94/27988. These compounds have improved pharmacokinetic and metabolic properties which will give an improved therapeutic profile such as a lower degree of interindividual variation. WO 96/02535 discloses a process for the preparation of the single enantiomers of omeprazole and salts thereof.

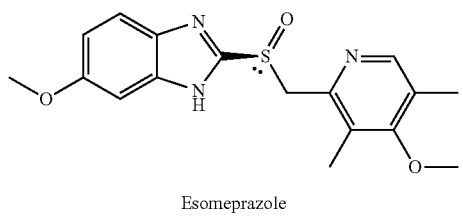

Formula IV

Esomeprazole

Pharmaceutical compositions that include one or more compounds obtained by the process aspect of the invention are also provided. In particular, in one variant, a pharmaceutical composition that includes the amorphous esomeprazole produced as described in U.S. Pat. No. 2004077869. The more preferred oral solid preparation is a tablet. A tablet may be prepared by direct compression, wet granulation, or molding, of the amorphous form of esomeprazole with a carrier and other excipients in a manner known to those skilled in the art. The amorphous form of esomeprazole described U.S. Pat. No. 2004077869 may be formulated into typical disintegrating tablet, or into a controlled or extended release dosage forms. Examples of suitable modified release formulation vehicles are disclosed in U.S. Pat. Nos. 3,845,770; 3,916,899; 3,536,809; 3,598,123; and 4,008,719. WO 96/01623 discloses suitable tableted dosage forms of for instance magnesium salts R- and S-omeprazole.

As described above, the major factor contributing to the development of gastrointestinal disorders is the presence of acid in the stomach and upper small intestine. Therefore, the main object of the invention is administering to a patient an oral dosage form including a combination of an antithrombotic agent and a proton pump inhibitor which can reduce a major factor contributing to the development of gastrointestinal disorder in patients. According to the main object, the pharmaceutical compositions of this invention is for the prevention gastrointestinal tract from side effects associated with antithrombotic therapy and provide greater antithrombotic effect with the results in a lower incidence of side effects. According to prior inventions dabigatran etexilate in combination with proton pump inhibitors in particular dexlansoprazole or esomeprazole have an additive preventive effect in relief of gastrointestinal disorder and provide greater antithrombotic effect with the results in a lower incidence of side effects.

According to the formulation of the present invention it is desired to provide a dosage form comprising in combination a therapeutically effective amount of an antithrombotic agent, specifically dabigatran and a proton pump inhibitor specifically dexlansoprazole or esomeprazole which overcomes above described problems. The main challenges when combining those molecules in the same pharmaceutical form are:

(a) to guarantee the psycho-chemical compatibility between those different active ingredients and/or between the active ingredients and the excipients used; and (b) to insure the therapeutical compatibility between those active ingredients regarding their stability characteristics.

When dabigatran etexilate is combined with PPI specifically dexlansoprazole or esomeprazole in order to minimize or prevent the side effects of the dabigatran etexilate, these two drug substances must be released, dissolved and absorbed harmoniously. For the efficiency of the formulation, an easy dissolution of both drug substances at a desired time is an important factor. In order to minimize or prevent the side effects of dabigatran etexilate; it is very important for the molecule, in which the molecule is used in combination with the PPIs to release both drug substances at the desired time.

DETAILED DESCRIPTION OF THE INVENTION

The present invention relates to a pharmaceutical composition comprising dabigatran or a pharmaceutically acceptable salt, solvate, hydrate, enantiomer, prodrug or polymorph thereof in a combination with a proton pump inhibitor or a pharmaceutically acceptable salt, solvate, hydrate, enantiomer, prodrug or polymorph thereof and at least one pharmaceutically acceptable excipient The main object of the present invention is to provide new pharmaceutical compositions comprising a specific direct thrombin inhibitor such as dabigatran etexilate in combination with proton pump inhibitors such as cinprazole, dexlansoprazole, disuprazole, esaprazole, esomeprazole, fuprazole, ilaprazole, lansoprazole, leminoprazole, levolansoprazole, nepaprazole, nilprazole, omeprazole, pantoprazole, picoprazole, pumaprazole, rabeprazole, saviprazole, tenatoprazole, timoprazole, ufiprazole or other benzimidazole derivatives or a pharmaceutically acceptable salt, solvate, hydrate, enantiomer, prodrug or polymorph thereof as effective components which overcomes the above described problems in prior art and have additive advantages over them.

The product in this invention, is used for protecting the gastrointestinal tract from side effects associated with antithrombotic therapy using the oral dosage forms described herein. The invention also relates to protect the gastrointestinal tract from side effects associated with antithrombotic therapy by combination an antithrombotic agent and a proton pump inhibitor. These and other features of the present invention are set forth herein more detailed.

In one embodiment, the proton pump inhibitor is preferably lansoprazole or omeprazole or an acceptable salt, solvate, hydrate, enantiomer, prodrug or polymorph thereof.

In one embodiment, the pharmaceutical composition comprises dabigatran or a pharmaceutically acceptable salt, solvate, hydrate, enantiomer, prodrug or polymorph thereof and lansoprazole or a pharmaceutically acceptable salt, solvate, hydrate, enantiomer, prodrug or polymorph thereof. In a preferred embodiment, lansoprazole is present in an amount of between 15 mg and 60 mg. In a more preferred embodiment, lansoprazole is present in an amount of between 15 mg and 30 mg.

In one embodiment, the pharmaceutical composition comprises dabigatran or a pharmaceutically acceptable salt, solvate, hydrate, enantiomer, prodrug or polymorph thereof in a combination with an enantiomer of lansoprazole which is dexlansoprazole. In a preferred embodiment, dexlansoprazole is present in an amount of between 10 mg and 75 mg. In a more preferred embodiment, dexlansoprazole is present in an amount of 20 mg.

In one embodiment, the pharmaceutical composition of the present invention comprises dabigatran or a pharmaceutically acceptable salt, solvate, hydrate, enantiomer, prodrug or polymorph thereof and omeprazole or a pharmaceutically acceptable salt, solvate, hydrate, enantiomer, prodrug or polymorph thereof. According to this embodiment, omeprazole is present in an amount of between 10 mg and 75 mg. In a more preferred embodiment, omeprazole is present in an amount of 20 mg.

In one embodiment, the pharmaceutical composition comprises dabigatran or a pharmaceutically acceptable salt, solvate, hydrate, enantiomer, prodrug or polymorph thereof in a combination with an enantiomer of omeprazole which is esomeprazole. In a preferred embodiment, esomeprazole is present in an amount of between 10 mg and 75 mg. In a more preferred embodiment, esomeprazole is present in an amount of 20 mg.

In a preferred embodiment, a pharmaceutically acceptable salt, solvate, hydrate, enantiomer, prodrug or polymorph of dabigatran is the etexilate or etexilate mesylate prodrugs of dabigatran. In another preferred embodiment dabigatran etexilate is present in an amount of between 50 and 250 mg.

In a preferred embodiment dabigatran etexilate or etexilate mesylate present in an amount of between 50 and 250 mg and the dexlansoprazole or a pharmaceutically acceptable salt, solvate, hydrate, enantiomer, prodrug or polymorph thereof is present in an amount of between 10 and 75 mg.

In another preferred embodiment dabigatran etexilate or etexilate mesylate present in an amount of between 50 and 250 mg and the esomeprazole or a pharmaceutically acceptable salt, solvate, hydrate, enantiomer, prodrug or polymorph thereof is present in an amount of between 10 and 75 mg.

According to main object of the invention, pharmaceutical formulations of dabigatran etexilate in a combination with a proton pump inhibitor have a good stability and have improved manufacturing process that is achieved in a technologically simple way which overcomes the above described problems.

Yet another object of the present invention is to provide an improved process which is simple, cost-effective and time saving for preparing the pharmaceutical composition of dabigatran or pharmaceutically acceptable salts thereof and one or more PPIs specially esomeprazole and dexlansoprazole.

In another embodiment, the oral formulations described herein can be used to treat, prevent or reduce the risk of almost any physiological disorder for which antithrombotic agents are indicated. The methods and formulations provided herein can be administered to any subject in need of therapy including, without limitation, humans, including patients, companion animals, including, but not limited to dogs, cats, ferrets, and birds, food-source animals, including, but not limited to cows, pigs, and sheep, and zoo animals, such as monkeys and other primates, and other similar animal species.

In one embodiment, these pharmaceutical combinations are administered oral, parenteral, intranasal, sublingual, transdermal, transmucosal, ophthalmic, intravenous, pulmonary, intramuscular or rectal administration, and preferably for oral administration. According to this embodiment of the invention, said pharmaceutical composition may be formulated with suitable pharmaceutical diluents, excipients or carriers, suitably selected with respect to a dosage form for oral administration. Examples of dosage forms include tablets, compressed tablets, coated tablets, uncoated tablets, multilayer tablets, buccal tablets, sublingual tablets, effervescent compositions, effervescent tablets, immediate release tablets, modified release tablets, film-coated tablets, orally disintegrating tablets, gastric disintegrating tablets, pills, capsules, hard or soft gelatin capsules, powders, mini tablets, pellets, coated bead systems, granules, microspheres, ion exchange resin systems, sterile solutions or suspensions, sterile ocular solutions, aerosols, sprays, drops, ampoules, suppositories, ocular systems, parenteral systems, creams, gels, ointments, dragees, sachets; films, orally administrable films, solutions, solids; elixirs, tinctures, suspensions, syrups, colloidal dispersions, dispersions, emulsions and thereof.

Another object of the invention is to provide a pharmaceutical composition for use in antithrombotic treatment and its use in reducing the risk of stroke and systemic embolism in patients with non-vascular atrial fibrillation and protecting the gastrointestinal tract from side effects associated with antithrombotic therapy.

In a preferred embodiment said pharmaceutical composition is formulated preferably in the form of tablet or capsule or multilayer tablet comprising etexilate or etexilate mesylate pellets of dabigatran and proton pump inhibitor pellets Dabigatran+PPI DSC Analysis DSC Analysis: DSC scan of about 2 mg using an automatic thermal analyzer system performed accurately weighed of APIs (Dabigatran etexilate, Dabigatran etexilate mesylate, Esomeprazole, Dexlansoprazole) of 1:1 in ratio respectively. DSC scans performed with 10° C. per minute heat flow from 30° C. to 300° C. The peak shifting of active ingredients was determined by DSC analysis.

Figure 2:
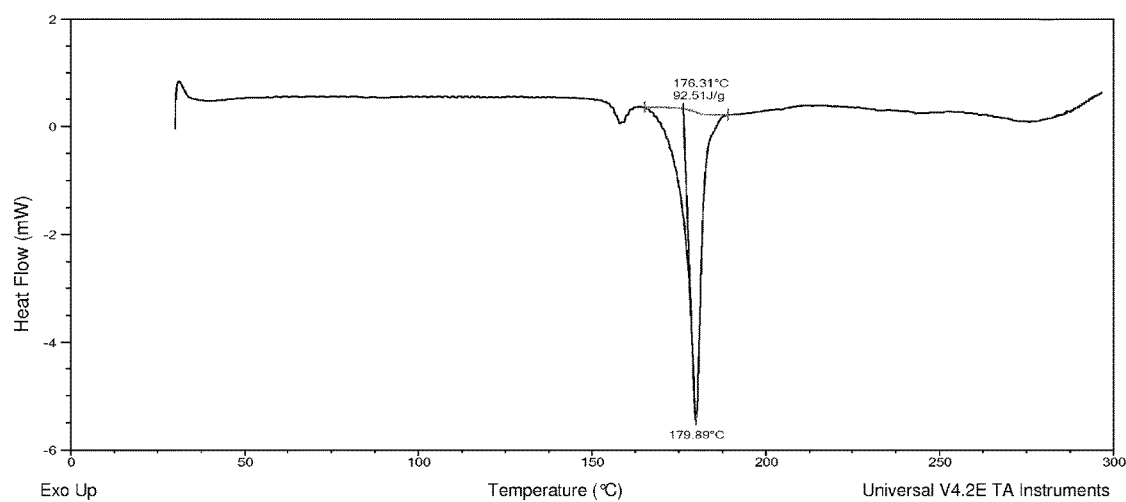
Figure 3:
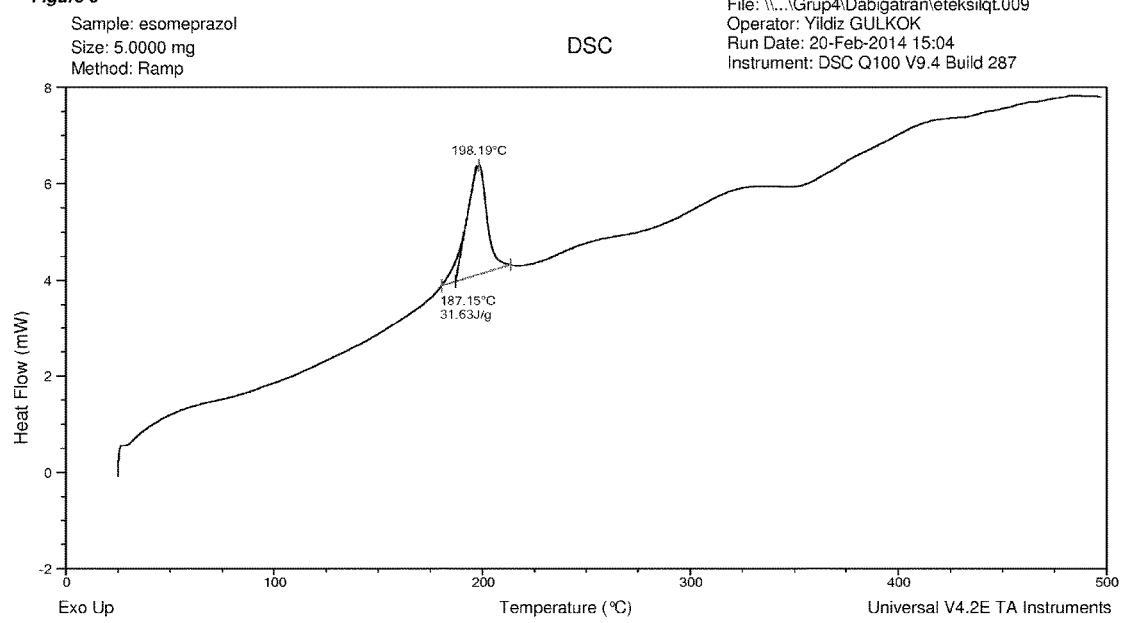
Figure 4:
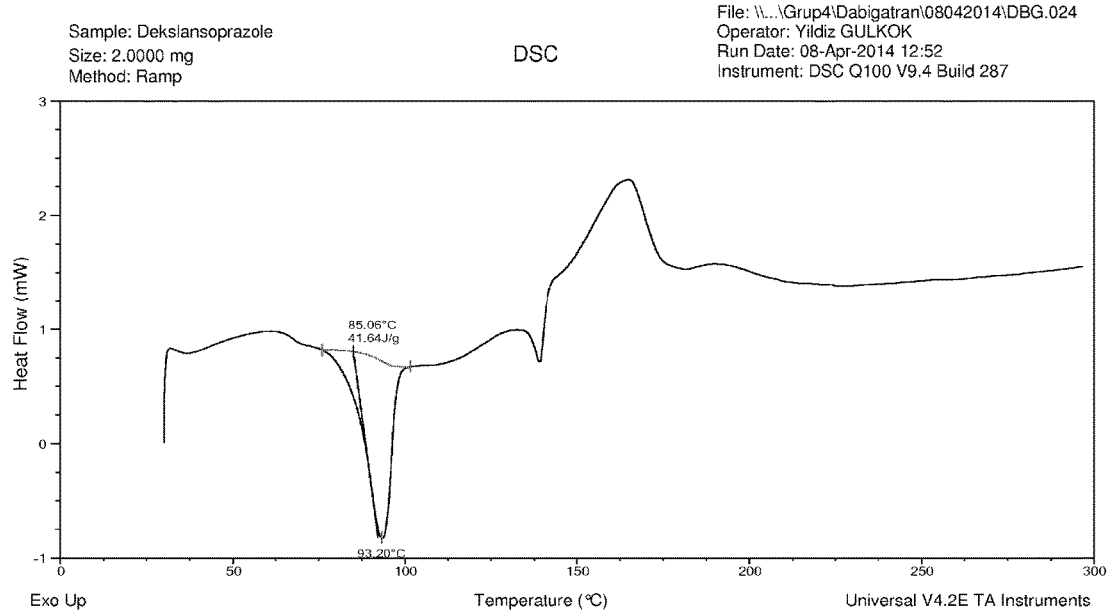
Figure 5:
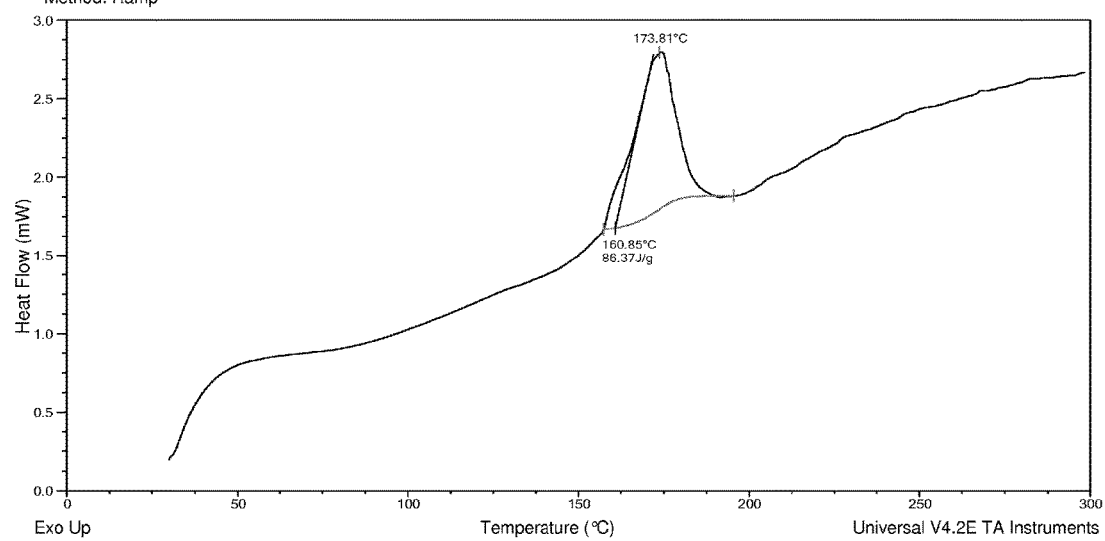
Figure 6:
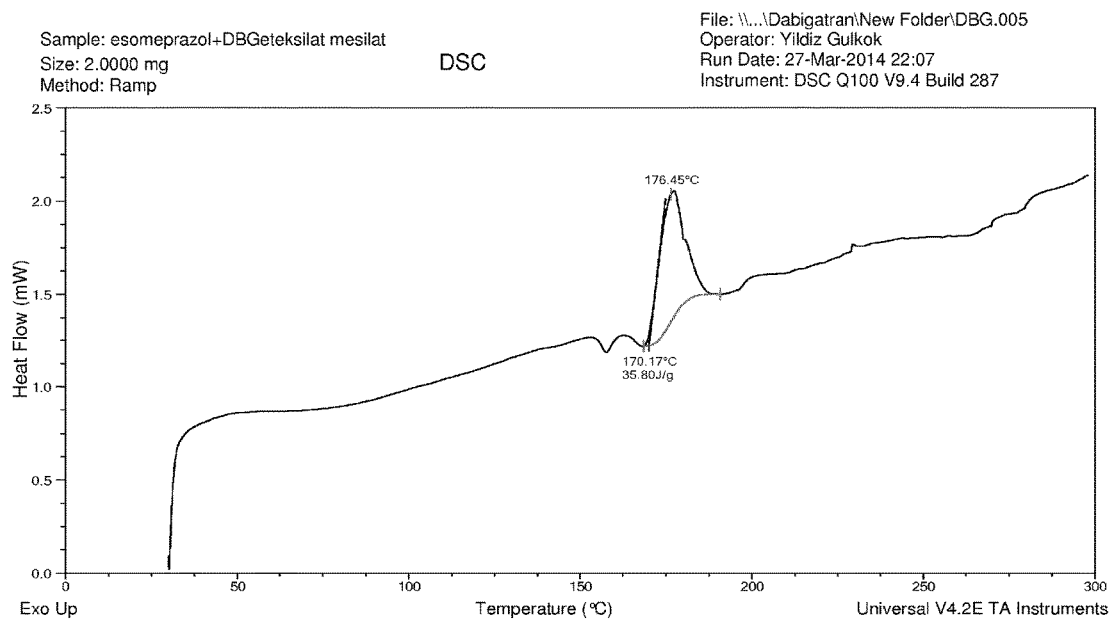
Figure 7:
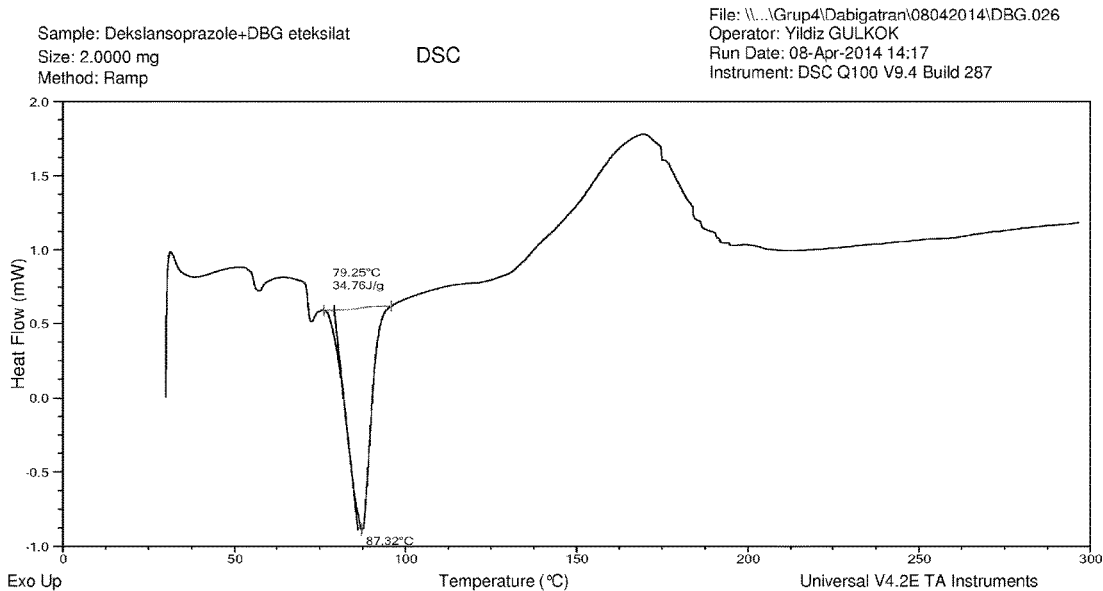
Figure 8:
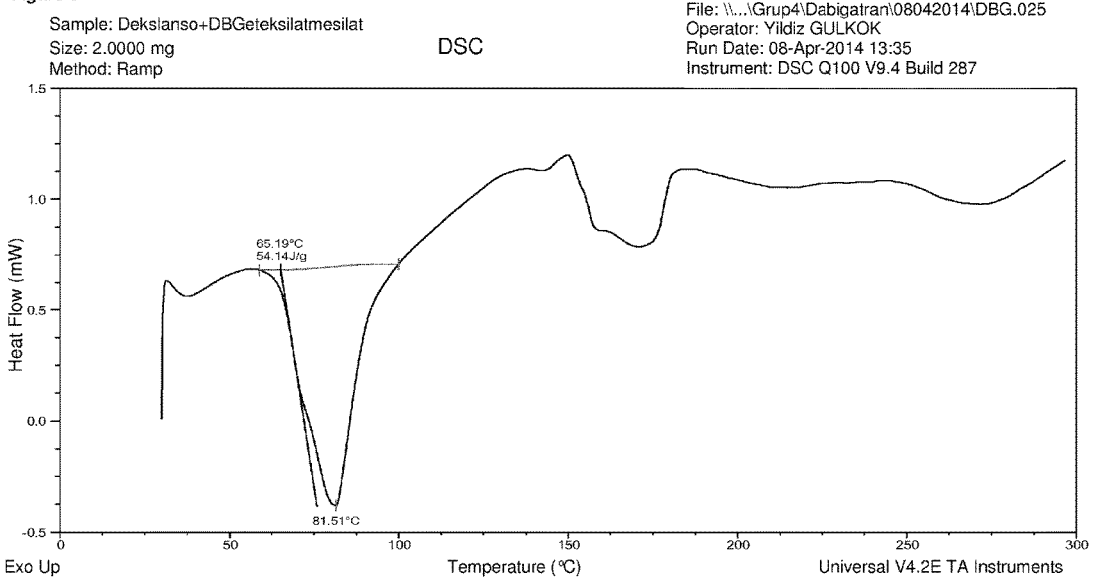

Method Log:
1: Pan Type: Aluminum hermetic
2: Equilibrate at 30.00° C.
3: Ramp 10.00 ° C./min to 300.00° C.
4: End of method Results (Thermograms):
FIG. 1. Thermogram of Dabigatran etexilate
FIG. 2. Thermogram of Dabigatran etexilate mesylate
FIG. 3. Thermogram of Esomeprazole
FIG. 4. Thermogram of Dexlansoprazole
FIG. 5. Thermogram of Dabigatran etexilate: Esomeprazole
FIG. 6. Thermogram of Dabigatran etexilate mesylate: Esomeprazole
FIG. 7. Thermogram of Dabigatran etexilate: Dexlansoprazole
FIG. 8. Thermogram of Dabigatran etexilate mesylate: Dexlansoprazole Discussion: The characteristic degradation and melting peaks of active ingredients were not determined. It indicates pharmaceutical incompatibility of esomeprazole and dexlansoprazole with Dabigatran etexilate and Dabigatran etexilate mesylate.

|  | Melting temperature (° C.) | Dabigatran etexilate | Dabigatran etexilate mesylate |
|---|---|---|---|
| Melting temperature (° C.) | — | 132 | 180 |
| Esomeprazole | 198 (Degradation) | 174 The characteristic degradation and melting peaks of both | 176 The characteristic degradation and melting peaks of both |

-continued

| | Melting temperature (° C.) | Dabigatran etexilate | Dabigatran etexilate mesylate |
|---|---|---|---|
| Dexlansoprazole | 93 | active ingredients were not determined, They're incompatible. 87 The characteristic melting peak of Dabigatran etexilate was not determined. They're incompatible. | active ingredients were not determined. They're incompatible. 82 The characteristic melting peak of Dabigatran etexilate mesylate was not determined. They're incompatible. |

According to the pharmaceutical incompatibility problem, the present invention provides a pharmaceutical composition comprising a barrier layer which is present in the middle in such a way that it separates dabigatran etexilate and one of the proton pump inhibitors layers and the dabigatran etexilate and PPI layers are present at the outer or inner part of the barrier layer. By the virtue of the barrier layer, interaction between the dabigatran etexilate and PPI molecules is prevented. Moreover, another important reason is that the formulations of the active substances with different release properties can be provided in the same form with barrier layer. In order to minimize gastric damage, enteric coated formulations such that controlled release thereof will be performed with the combination with a barrier layer.

In one embodiment of the invention, the bilayer or multilayer tablet may comprise optionally a barrier layer between the two layers wherein the barrier layer is selected from the group consisting of corn starch, lactose, sugar alcohol (D-mannitol, erythritol, etc.), low substituted hydroxypropyl cellulose, hydroxypropyl cellulose, hydroxypropyl methylcellulose, polyvinylpyrrolidone, polyvinyl alcohol, methylcellulose, hydroxyethyl methylcellulose or mixtures thereof. Thus, the multilayer tablet according to the present invention has two or more layers comprising the dabigatran etexilate and PPI molecules seperately and it is characterized in releasing these molecules together and rapidly. The multilayer tablet according to the present invention is formulated in such a way that it increases the pH of the stomach by the dissolution of PPI after the dissolution of dabigatran etexilate that provides less gastrointestinal damage.

According to the challenges mentioned above the selection of the excipients thus very important. According to this embodiment, one or more pharmaceutically acceptable excipient is selected from the group comprising buffering agents, stabilizers, binders, diluents, dispersing agents, lubricants, glidants, disintegrants, plasticizers, preservatives, sweeteners, flavoring agents, coloring agents, wetting agents, emulsifiers, acids or mixtures thereof.

In a preferred embodiment, said pharmaceutical composition comprises an acid which is selected from a group comprising organic acids or inorganic acids or mixtures thereof Suitable organic acids may comprise but not limited to acetic acid, acrylic acid, adipic acid, aldaric acid, ascorbic acid, azelaic acid, benzoic acid, butyric acid, chloroacetic acid, citric acid, crotonic acid, dimercaptosuccinic acid, formic acid, fumaric acid, gallic acid, glutaric acid, itaconic acid, lactic acid, malic acid, maleic acid, malonic acid, monanoic acid, methacrylic acid, naphtenic acid, oleic acid, oxalic acid, palmitic acid, paracetic acid, propionic acid, pimelic acid, salicylic acid, sebacic acid, succinic acid, stearic acid, sorbic acid, tartaric acid, thiomalic acid, uric acid, glyceric acid, xylonic acid, gluconic acid, neuraminic acid, ulosonic acid, ketodeoxyoctulosonic acid, glucuronic acid, galacturonic acid, iduronic acid, meso-galactaric acid, mucic acid, d-glucaric acid, saccharic acid, glycolic acid, mandelic acid, aspartic acid, glutamic acid, and the like or mixtures thereof.

Organic acids are preferably lactic acid, acetic acid, formic acid, oxalic acid, uric acid, carboxylic acid (adipic acid (dicarboxylic), azelaic acid, butyric acid, crotonic acid, gallic acid, itaconic acid, oleic acid, palmitic acid, propionic acid, sebacic acid, sorbic acid), sugar acid (glyceric acid (3C ), xylonic acid (5C ), gluconic acid (6C ), ulosonic acids), aldaric acids (meso-galactaric acid (mucic acid) (6C ), D-glucaric acid (saccharic acid) (6C ), mandelic acid) for pharmaceutical composition.

Suitable inorganic acids may comprise but not limited to hydrogen halides and their solutions: hydrofluoric acid (HF), hydrochloric acid (HCl), hydrobromic acid (HBr), hydroiodic acid (Hl); halogen oxoacids: hypochlorous acid (HClO), chlorous acid (HClO2), chloric acid (HClO3), perchloric acid (HClO4), and corresponding compounds for bromine and iodine; sulfuric acid (H2SO4), fluorosulfuric acid (HSO3F), nitric acid (HNO3), phosphoric acid (H3PO4), fluoroantimonic acid (HSbF6), fluoroboric acid (HBF4), hexafluoro phosphoric acid (HPF6), chromic acid (H2CrO4), boric acid (H3BO3) and the like or mixtures thereof.

Inorganic acids are preferably hydrogen halides (hydrofluoric acid (HF), hydrobromic acid (HBr), hydroiodic acid (Hl)), halogen oxoacids (hypochlorous acid (HClO), and corresponding compounds for bromine and iodine), nitric acid (HNO3), fluoroboric acid (HBF4), chromic acid (H2CrO4) for pharmaceutical composition.

Suitable buffering agents may comprise but not limited to alkali metal citrate, citric acid/sodium citrate, tartaric acid, fumaric acid, sorbic acid, citric acid, succinic acid, adipic acid, ascorbic acid, glutaric acid, potassium hydrogen tartrate, sodium hydrogen tartrate, potassium hydrogen phthalate, sodium hydrogen phthalate, potassium dihydrogen phosphate, sodium dihydrogen phosphate, disodium hydrogen phosphate, hydrochloric acid/sodium hydroxide or mixtures thereof, and preferably citric acid, fumaric acid, ascorbic acid, sodium dihydrogen phosphate and the like or mixtures thereof.

Suitable stabilizers may comprise but not limited to citric acid, fumaric acid, tartaric acid, sodium citrate, sodium benzoate, sodium dihydrogen phosphate, calcium carbonate, magnesium carbonate, arginine, lysine, meglamine, tocopherol, butylhydroxyanisole (BHA), butylhydroxytoluene (BHT), ascorbic acid, gallic acid esters or the mixtures thereof, and preferably, citric acid, fumaric acid, arginine and the like or mixtures thereof.

Suitable binders may include but not limited to polyvinylpyrrolidone, polyethylene glycol, polyvinyl alcohol, starch, pregelatinized starch, glucose, glucose syrup, natural gums, sucrose, sodium alginate, cellulose derivatives such as hydroxypropyl methyl cellulose, hydroxypropyl cellulose, carboxy methyl cellulose, methyl cellulose, gelatin, carrageenan, guar gum, carbomer, polymethacrylates, methacrylate polymers, collagens, proteins like gelatin, agar, alginate, alginic acid, xanthan gum, hyaluronic acid, pectin, polysaccharides, carbomer, poloxamer, polyacrylamide, aluminium hydroxide, laponit, bentonit, polyoxyethylene-alkyl ether, polydextrose, polyethylene oxide and the like or mixtures thereof.

Suitable diluents may comprise but not limited to microcrystalline cellulose, mannitol, spray-dried mannitol, lactose, starch, dextrose, sucrose, fructose, maltose, sorbitol, xylitol, inositol, kaolin, inorganic salts, calcium salts, polysaccharides, dicalcium phosphate, sodium chloride, dextrates, lactitol, maltodextrin, sucrose-maltodextrin mixture, trehalose, sodium carbonate, sodium bicarbonate, calcium carbonate and the like or mixtures thereof.

Suitable dispersing agents may comprise but not limited to calcium silicate, magnesium aluminum silicate and the like or mixtures thereof.

Suitable lubricants may comprise but not limited to magnesium stearate, calcium stearate, zinc stearate, talc, waxes, boric acid, hydrogenated vegetable oil, sodium chlorate, magnesium lauryl sulfate, sodium oleate, sodium acetate, sodium benzoate, polyethylene glycol, stearic acid, fatty acid, fumaric acid, glyseryl palmito sulphate, sodium stearyl fumarate, sodium lauryl sulphate and the like or mixtures thereof.

Suitable glidants may comprise but not limited to talc, aluminium silicate, colloidal silica, starch and the like or mixtures thereof.

Suitable disintegrants may comprise but not limited to cross-linked polyvinil pyrrolidone (crospovidone), povidone, cross-linked carboxymethyl cellulose (croscarmellose sodium), low-substituted hydroxypropyl cellulose, pregelatinized starch, sodium carboxymethyl cellulose, calcium carboxymethyl cellulose, carboxymethyl cellulose, docusate sodium, guar gum, low substituted hydroxypropyl cellulose, polyacryline potassium, sodium alginate, corn starch, sodium starch glycolate, alginic acid, alginates, ion-exchange resins, magnesium aluminium silica, sodium dodesyl sulphate, poloxamer, sodium glycine carbonate, sodium lauryl sulphate and the like or mixtures thereof.

Suitable plasticizers may comprise but not limited to polyethylene glycols of different molecular weights, propylene glycol and the like or mixtures thereof.

Suitable preservatives may comprise but not limited to methyl paraben, propyl paraben and their salts (such as sodium, potassium), sodium benzoate, citric acid, benzoic acid, butylated hydroxytoluene or butylated hydroxyanisole and the like or mixtures thereof.

Suitable sweeteners may comprise but not limited to aspartame, potassium acesulfame, sodium saccharinate, neohesperidine dihydrochalcone, sucralose, saccharin, sugars such as sucrose, glucose, lactose, fructose or sugar alcohols such as mannitol, sorbitol, xylitol, erythritol and the like or mixtures thereof.

Suitable flavorings may comprise but not limited to menthol, peppermint, cinnamon, chocolate, vanillin or fruit essences such as cherry, orange, strawberry, grape, black currant, raspberry, banana, red fruits, wild berries and the like or mixtures thereof.

Suitable coloring agents may comprise but not limited to ferric oxide, titanium dioxide, Food, Drug & Cosmetic (FD&C) dyes (such as; FD&C blue, FD&C green, FD&C red, FD&C yellow, FD&C lakes), poncau, indigo Drug & Cosmetic (D&C) blue, indigotine FD&C blue, carmoisine indigotine (indigo Carmine); iron oxides (such as; iron oxide red, yellow, black), quinoline yellow, flaming red, carmine, carmoisine, sunset yellow and the like or mixtures thereof.

In a preferred embodiment of the present invention, said pharmaceutical composition is in the form of tablet or capsule or multilayer tablet comprising etexilate or etexilate mesylate of dabigatran pellets and proton pump inhibitor pellets and acid pellets which are separate pellets or bilayer or multilayer pellets.

In a preferred embodiment of the present invention said dabigatran pellets comprising preferably methacrylic acid-ethyl acrylate copolymer (Eudragit EPO) or polyvinyl alcohol (PVA) or lactose monohydrate or sugar pellet or polyvinylpyrrolidone (PVP) or dibasic calcium phosphate (DCP) or mixtures thereof as pharmaceutically acceptable excipients In a preferred embodiment of the present invention said acid pellets comprising preferably adipic acid or sorbic acid or succinic acid or glutaric acid or nitric acid and as an excipient xanthan gum or isopropyl alcohol (IPA) or sodium alginate or microcrystalline cellulose or mannitol or lactose or silicon dioxide or methacrylic acid-ethyl acrylate copolymer (Eudragit EPO) or polyvinyl alcohol (PVA) or mixtures thereof In a preferred embodiment of the present invention said proton pump inhibitor pellets comprising preferably sugar pellet or mannitol or sodium starch glycolate or magnesium carbonate or povidone K30 or sucrose or poloxamer 407 or polyvinyl alcohol (PVA) or methacrylic acid- ethyl acrylate copolymer or talc or triethyl citrate or simethicone emulsion or dibasic calcium phosphate (DCP) or polyvinylpyrrolidone (PVP) or methacrylic acid-ethyl acrylate copolymer (Eudragit L100-55) or kollicoat MAE 30DP or polyvinyl acetate (kollidon SR) or dibasic calcium phosphate (DCP) or mixtures thereof as pharmaceutically acceptable excipients When these compounds are formulated into pharmaceutical preparations for oral administration, they require special techniques to avoid contact of PPIs with gastric acid of the stomach. One technique most commonly used is to coat these compounds, or its granules or pellets, with an enteric coating. However, the material used in enteric coatings itself is acidic, which can cause the decomposition of the compound. Such decomposition occurs even during the enteric coating process, which results in the coloration of the surface of the drug-containing core.

Enteric films do not show high flexibility so that compression stress can yield rupturing of the film. It is therefore necessary to use a tableting technique that endorses the compression strain and maintains the acid resistance of the formulation after compression of the granules. Therefore caution is needed to be taken while compressing the tablets especially to form bilayer dosage form.

In other embodiments, the enteric coating surrounds the antithrombotic agent in the oral dosage form. In still another embodiment, the enteric coating surrounds both the proton pump inhibitor and the antithrombotic agent in the oral dosage form. In some embodiments, the enteric coating surrounds essentially all of the proton pump inhibitor. In other embodiments, the enteric coating surrounds essentially all of the antithrombotic agent. In still other embodiments, the enteric coating surrounds essentially all of both the proton pump inhibitor and the antithrombotic agent in the oral dosage form. In other embodiments, the oral dosage form does not include an enteric coating. In other embodiments, the oral dosage form is substantially free of an enteric coating.

In a preferred embodiment of the present invention said proton pump inhibitor pellets comprises enteric coating in an amount of 1% to 20% (w/w) of the total weight of the pellets preferably in an amount of 2% to 10% (w/w) wherein the enteric coating dissolves at pH 5.5 or higher.

According to this embodiment, the enteric polymers of the enteric coating layer composition can be selected from the group comprising of cellulose acetate phthalate, cellulose acetate succinate, hydroxpropyl cellulose, hydroxpropyl cellulose phthalate, hydroxpropyl ethylcellulose, hydroxpropyl ethylcellulose phthalate, hydroxyl propyl methyl cellulose, hydroxyl propyl methyl cellulose phthalate, hydroxyl propyl methyl cellulose acetate succinate, hydroxyethyl cellulose phthalate, methylcellulose phthalate, polyvinyl acetate, polyvinyl acetate phthalate, polyvinylacetate hydrogen phthalate, cellulose ester phthalates, cellulose ether phthalates, sodium cellulose acetate phthalate, starch, starch acid phthalate, cellulose acetate butyrate, cellulose acetate maleate, cellulose acetate trimellitate, cellulose acetate propionate, cellulose acetate phthalate, styrene maleic acid dibutyl phthalate copolymer, styrene maleic acid polyvinyl acetate phthalate copolymer, ammonium methacrylate copolymers, hydrogels, carboxyvinyl polymer, sodium alginate, sodium carmellose, calcium carmellose, polyvinyl alcohol, polyvinyl alcohol-polyethylene glycol mixtures, gelatine, polyvinylpyrrolidone, microcrystalline cellulose, collagen, ethyl cellulose, carboxymethyl cellulose, carnauba wax, pectin, carbomer, poloxamer, polyachrylamide, aluminium hydroxide, bentonit, laponit, setostearyl alcohol, polyoxyethylen-alkyl ethers, hyaluronic acid, guar gum, cocoa oil, paraffin, hydrogenated vegetable oil, cetyl alcohol, stearyl alcohol, stearic acid, xanthane gum, shellac or mixtures thereof.

According to the pharmaceutical compositions of the invention may be prepared by conventional technology well known to those skilled in the art such as direct compression, dry granulation, wet granulation and the like. During direct compression, active agent and excipients are mixed, sieved and compressed into dosage forms.

During wet granulation, the ingredients are mixed and granulated with a granulation liquid. The granulation process provides agglomerates with a desired homogeneity. The mixture is dried and sieved and optionally mixed with additional excipients. Finally, it is compressed into dosage forms. In addition, this novel pharmaceutical formulation is produced by various technologies such as fluidized bed granulation technique or extrusion/spheronization or spray drying and lyofilization.

EXAMPLES

Example 1

Multilayer Core Pelletization (Organic acid pellets are Coated with Dabigatran+PPI Pellets)

Multilayer Pellets (Organic Acid Pellets are Coated with Dabigatran):
%5.0-95 Adipic acid or Sorbic acid or Succinic acid or Glutaric acid
%0.05-50 Xanthan gum
%0.05-20 Polyvinyl alcohol (PVA) or isopropyl alcohol (IPA)
%0.05-20 Sodium alginate
%15.0-60 Dabigatran etexilate mesylate (DEM)
%0.5-40 Methacrylic acid-Ethyl acrylate copolymer (Eudragit EPO) or PVA PPI Pellets:
%2.0-30 Esomeprazole or Dexlansoprazole
%5.0-90 Sugar Pellet
%10.0-80 Mannitol
%0.05-10 Sodium starch glycolate
%0.5-30 Magnesium carbonate
%0.05-30 Povidone K30
%0.05-30 Sucrose
%0.05-30 Poloxamer 407
%0.05-50 Polyvinyl alcohol (PVA)
%0.5-40 Methacrylic acid Ethyl acrylate copolymer (1:1) dispersion 30%
%0.5-30 Talc
%0.02-20 Triethyl citrate
%0.00-5 Simethicone emulsion Other Excipients:
%0.1-0.2 Silicon dioxide
%0.25-2.0 Magnesium stearate Production process of multilayer pellets (organic acid pellets are coated with Dabigatran): Adipic acid or Sorbic acid or Succinic acid or Glutaric acid and Xanthan gum are mixed together. Alcoholic PVA or IPA (isopropyl alcohol) solution is sprayed onto this mixture and pellets produced by fluidized bed pelletizing technique. The pellets are coated with sodium alginate in fluidized bed so acid pellets are manufactured. DEM is dissolved in alcoholic Methacrylic acid-Ethyl acrylate copolymer (Eudragit EPO) or Polyvinyl alcohol (PVA) solution. This solution is sprayed onto the acid pellet by fluidized bed pelletizing technique so multilayer pellets are manufactured.

Production process of PPI pellets: Esomeprazole/Dexlansoprazole, mannitol, sodium starch glycolate, magnesium carbonate, povidone K30 and sucrose are mixed together. Poloxamer 407 and alcoholic PVA solution are added to this mixture. This solution/dispersion is sprayed onto the sugar pellets. Methacrylic acid: Ethyl acrylate copolymer (1:1) dispersion (30%) is prepared with talc, triethyl sitrate, simethicone emulsion. This pellets are coated by spraying this mixture.

The multilayer and PPI pellets first mixed with silicon dioxide and then with magnesium stearate. Finally, the pellets are pressed as tablets or filled into the capsules.

Example 2

Multilayer Core Pelletization (Dabigatran Pellets are Coated with Organic Acid+PPI Pellets)

Multilayer Pellets (Dabigatran Pellets are Coated with Organic Acid):
%15.0-60 Dabigatran etexilate mesylate (DEM)
%0.5-40 Methacrylic acid-Ethyl acrylate copolymer (Eudragit EPO) or Polyvinyl alcohol (PVA)
%5.0-40 Lactose monohydrate
%5.0-95 Adipic acid or Sorbic acid or Succinic acid or Glutaric acid
%0.05-50 Xanthan gum PPI pellets:
%2.0-30 Esomeprazole or Dexlansoprazole
%5.0-40 Dibasic calcium phosphate (DCP)
%0.1-25 Polyvinylpyrrolidone (PVP)
%0.5-40 Polyvinyl alcohol (PVA)
Other Excipients:
%0.1-0.2 Silicon dioxide
%0.25-2.0 Magnesium stearate Production process of multilayer pellets (Dabigatran pellets are coated with organic acid): DEM and lactose monohydrate are mixed together. Alcoholic Methacrylic acid-Ethyl acrylate copolymer (Eudragit EPO) or Polyvinyl alcohol (PVA) solution is sprayed onto this mixture and pellets produced by fluidized bed pelletizing technique. The solution is prepared by adding adipic acid or sorbic acid or succinic acid or glutaric acid and xanthan gum. This solution is sprayed onto the DEM pellets by fluidized bed pelletizing technique so multilayer pellets are manufactured.

Production process of PPI pellets: Esomeprazole/Dexlansoprazole and DCP and PVP are blended, then by spraying PVA alcoholic/hydroalcoholic solution a wet mass is formed, Pellets produced from this wet mass by extrusion/spheronization pelletizing technique. The pellets are coated by PVA solution in fluidized bed.

The multilayer and PPI pellets first mixed with silicon dioxide and then with magnesium stearate. Finally, the pellets are pressed as tablets or filled into the capsules.

Example 3

Coated Core Pelletization (Dabigatran Pellets+Inorganic Acid Pellets+PPI Pellets)

Inorganic Acid Pellets:
%0.05-10 Nitric acid
%5.0-40 Microcrystalline cellulose (MCC) or Mannitol or Lactose
%0.1-0.2 Silicon dioxide
%0.5-40 Methacrylic acid-Ethyl acrylate copolymer (Eudragit EPO) or Polyvinyl alcohol (PVA)
Dabigatran Pellets
%15.0-60 Dabigatran etexilate mesylate (DEM)
%5-90 Sugar pellet
%0.1-25 Polyvinylpyrrolidone (PVP)
%0.5-40 Methacrylic acid-Ethyl acrylate copolymer (Eudragit EPO or Polyvinyl alcohol (PVA)
PPI Pellets
%2.0-30 Esomeprazole or Dexlansoprazole
%5.0-90 Sugar pellet
%0.1-25 Polyvinylpyrrolidone (PVP)
%0.5-40 Methacrylic acid-Ethyl acrylate copolymer (Eudragit L100-55 or Kollicoat MAE 30DP)
%0.5-40 Polyvinyl acetate (Kollidon SR)
Other Excipients
%0.1-0.2 Silicon dioxide
%0.25-2.0 Magnesium stearate Production process of inorganic acid pellets: microcrystalline cellulose or mannitol or lactose and silicon dioxide are blended, then by spraying dilute nitric acid soution a wet mass is formed by high shear granulator or fluid bed granulator. The pellets are coated by Methacrylic acid-Ethyl acrylate copolymer (Eudragit EPO) or Polyvinyl alcohol (PVA) solution in fluidized bed so inorganic acid pellets are manufactured.

Production process of dabigatran pellets: Alcoholic solution/dispersion is prepared by adding DEM and PVP. Sugar pellets are coated with this solution/dispersion. The sugar pellets which were coated with the active ingredient are coated with Methacrylic acid-Ethyl acrylate copolymer (Eudragit EPO) or Polyvinyl alcohol (PVA) and then with PVA solution so DEM pellets are manufactured.

Production process of PPI pellets: Alcoholic solution/dispersion is prepared by adding Esomeprazole/Dexlansoprazole and PVP. Sugar pellets are coated with this solution/dispersion. The sugar pellets which were coated with the active ingredient are coated with Methacrylic acid-Ethyl acrylate copolymer (Eudragit L100-55 or Kollicoat MAE 30DP) and Polyvinyl acetate (Kollidon SR) and then with PVA solution so PPI pellets are manufactured.

Coated PPI pellets and DEM pellets and inorganic acid pellets are mixed. The pellets are first mixed with silicon dioxide and then with magnesium stearate. Finally, the pellets are pressed as tablets or filled into the capsules Example 4

Multilayer Combination Pellet (Multilayer Pellet Production)

%2.0-30 Esomeprazole orDexlansoprazole
%5.0-90 Sugar pellet
%0.1-25 Polyvinylpyrrolidone (PVP)
%0.5-40 Methacrylic acid-Ethyl acrylate copolymer (Eudragit L100-55 or Kollicoat MAE 30DP)
%0.5-40 Polyvinyl acetate (Kollidon SR)
%15.0-60 Dabigatran etexilate mesylate (DEM)
%0.5-40 Methacrylic acid-Ethyl acrylate copolymer (Eudragit EPO) or Polyvinyl alcohol (PVA)
%5.0-40 Lactose monohydrate
%5.0-95 Adipic acid or Sorbic acid or Succinic acid or Glutaric acid)
%0.05-50 Xanthan gum
%0.05-20 PVA
%0.1-0.2 Silicon dioxide
%0.25-2.0 Magnesium stearate Production process multilayer pellets: Alcoholic solution/dispersion is prepared by adding Esomeprazole/Dexlansoprazole and PVP. Sugar pellets are coated with this solution/dispersion. The sugar pellets which were coated with the active ingredient are coated with Methacrylic acid-Ethyl acrylate copolymer (Eudragit L100-55 or Kollicoat MAE 30DP) and Polyvinyl acetate (Kollidon SR) and then with PVA solution so PPI pellets are manufactured. DEM and lactose monohydrate are mixed with alcoholic Methacrylic acid-Ethyl acrylate copolymer (Eudragit EPO) or Polyvinyl alcohol(PVA) solution. This mixture is sprayed onto PPI pellets. The solution is prepared by adding adipic acid or sorbic acid or succinic acid or glutaric acid) and xanthan gum. This solution is sprayed onto the pellets so multilayer pellets are manufactured.

Finally the multilayer pellets are coated by PVA. The multilayer pellets first mixed with silicon dioxide and then with magnesium stearate. Finally, the pellets are pressed as tablets or filled into the capsules.

Example 5

Multilayer Combination Pellet (Multilayer Tablet Press)

Multilayer Pellets (Dabigatran Pellets are Coated with Organic Acid):
%15.0-60 Dabigatran etexilate mesylate (DEM)
%0.5-40 Methacrylic acid-Ethyl acrylate copolymer (Eudragit EPO) or Polyvinyl alcohol(PVA)

%5.0-40 Laktoz monohidrat
%5.0-95 Adipic acid or Sorbic acid or Succinic acid or Glutaric acid
%0.05-50 Xanthan gum
%0.05-20 PVA
PPI Pellets:
%2.0-30 Esomeprazole/Dexlansoprazole
%5.0-90 Sugar pellet
%0.1-25 Polyvinylpyrrolidone (PVP)
%0.5-40 Methacrylic acid-Ethyl acrylate copolymer (Eudragit L100-55 or Kollicoat MAE 30DP)
%0.5-40 Polyvinyl acetate (Kollidon SR)
%0.1-0.2 Silicon dioxide
%0.25-2.0 Magnesium stearate Production process of multilayer pellets (Dabigatran pellets are coated with organic acid): DEM and lactose monohydrate are mixed together. Alcoholic Methacrylic acid-Ethyl acrylate copolymer (Eudragit EPO) or Polyvinyl alcohol(PVA)solution is sprayed onto this mixture and pellets produced by fluidized bed pelletizing technique. The solution is prepared by adding adipic acid (or sorbic acid, succinic acid, glutaric acid) and xanthan gum. This solution is sprayed onto the DEM pellets by fluidized bed pelletizing technique so multilayer pellets are manufactured Production process of PPI pellets: Alcoholic solution/dispersion is prepared by adding Esomeprazole/Dexlansoprazole and PVP. Sugar pellets are coated with this solution/dispersion. The sugar pellets which were coated with the active ingredient are coated with Methacrylic acid-Ethyl acrylate copolymer (Eudragit L100-55 or Kollicoat MAE 30DP) and Polyvinyl acetate (Kollidon SR) and then with PVA solution so PPI pellets are manufactured.

The multilayer and PPI pellets first mixed with silicon dioxide and then with magnesium stearate. Finally, the pellets are pressed by multilayer rotary tablet press machine. Or dry coating-intertwined tablets which have PPI pellets on the core are produced with special tablet press machine.

The invention claimed is:

1. A multilayer pharmaceutical composition, said composition comprising: a first layer comprising dabigatran or a pharmaceutically acceptable salt, solvate, hydrate, enantiomer, prodrug or polymorph thereof; a second layer comprising a proton pump inhibitor or a pharmaceutically acceptable salt, solvate, hydrate, enantiomer, prodrug or polymorph of the proton pump inhibitor; and at least one pharmaceutically acceptable excipient, wherein the dissolution of the proton pump inhibitor occurs after the dissolution of dabigatran.

2. The pharmaceutical composition according to claim 1, wherein the proton pump inhibitor is a member selected from the group consisting of cinprazole, dexlansoprazole, disuprazole, esaprazole, esomeprazole, fuprazole, ilaprazole, lansoprazole, leminoprazole, levolansoprazole, nepaprazole, nilprazole, omeprazole, pantoprazole, picoprazole, pumaprazole, rabeprazole, saviprazole, tenatoprazole, timoprazole, ufiprazole, and a pharmaceutically acceptable salt, solvate, hydrate, enantiomer, prodrug or polymorph thereof.

3. The pharmaceutical composition according to claim 2, wherein the proton pump inhibitor is lansoprazole, omeprazole, or an acceptable salt, solvate, hydrate, enantiomer, prodrug or polymorph of lansoprazole or omeprazole.

4. The pharmaceutical composition according to claim 3, wherein the proton pump inhibitor is lansoprazole or a pharmaceutically acceptable salt, solvate, hydrate, enantiomer, prodrug or polymorph thereof.

5. The pharmaceutical composition according to claim 4, wherein the proton pump inhibitor is an enantiomer of lansoprazole, and the enantiomer of lansoprazole is dexlansoprazole.

6. The pharmaceutical composition according to claim 3, wherein the proton pump inhibitor is omeprazole or a pharmaceutically acceptable salt, solvate, hydrate, enantiomer, prodrug or polymorph thereof.

7. The pharmaceutical composition according to claim 6, wherein the proton pump inhibitor is an enantiomer of omeprazole, and the enantiomer of omeprazole is esomeprazole.

8. The pharmaceutical composition according to claim 1, wherein dabigatran or the pharmaceutically acceptable salt, solvate, hydrate, enantiomer, prodrug or polymorph thereof is dabigatran etexilate or dabigatran etexilate mesylate.

9. The pharmaceutical composition according to claim 5, wherein dabigatran or the pharmaceutically acceptable salt, solvate, hydrate, enantiomer, prodrug or polymorph thereof is dabigatran etexilate or dabigatran etexilate mesylate present in an amount of between 50 and 250 mg and the dexlansoprazole or a pharmaceutically acceptable salt, solvate, hydrate, enantiomer, prodrug or polymorph of dexlansoprazole is present in an amount of between 10 and 75 mg.

10. The pharmaceutical composition according to claim 7, wherein dabigatran or the pharmaceutically acceptable salt, solvate, hydrate, enantiomer, prodrug or polymorph thereof is dabigatran etexilate or dabigatran etexilate mesylate present in an amount of between 50 and 250 mg and the esomeprazole or a pharmaceutically acceptable salt, solvate, hydrate, enantiomer, prodrug or polymorph of esomeprazole is present in an amount of between 10 and 75 mg.

11. The pharmaceutical composition of claim 1, wherein said multilayer pharmaceutical composition is formulated as tablets, compressed tablets, coated tablets, uncoated tablets, modified release tablets, film-coated tablets, orally disintegrating tablets, gastric disintegrating tablets, pills, capsules, mini tablets, pellets, coated bead systems, granules, suppositories, dragees, solids, colloidal dispersions, dispersions, emulsions, or mixtures thereof.

12. A method of treating thrombosis in a subject with the pharmaceutical composition of claim 1, comprising administering an effective amount of the pharmaceutical composition to the subject in need thereof, wherein the risk of stroke and systemic embolism is reduced when the subject has non-vascular atrial fibrillation and the gastrointestinal tract is protected from side effects associated with antithrombotic therapy.

13. The pharmaceutical composition according to claim 11, wherein said multilayer pharmaceutical composition is formulated in the form of (i) a tablet or (ii) a capsule or (iii) a multilayer tablet, wherein (i), (ii) or (iii) comprise etexilate or etexilate mesylate pellets of dabigatran and proton pump inhibitor pellets.

14. The pharmaceutical composition of claim 1, wherein the one or more pharmaceutically acceptable excipients is a member selected from the group consisting of buffering agents, stabilizers, binders, diluents, dispersing agents, lubricants, glidants, disintegrants, plasticizers, preservatives, sweeteners, flavoring agents, coloring agents, wetting agents, emulsifiers, acids, and mixtures thereof.

15. The pharmaceutical composition according to claim 14, wherein said one or more pharmaceutically acceptable excipients comprise an acid which is a member selected from the group consisting of organic acids or inorganic acids, and mixtures thereof.

16. The pharmaceutical composition according to claim 15, wherein the organic acid is a member selected from the group consisting of acetic acid, acrylic acid, adipic acid, aldaric acid, ascorbic acid, azelaic acid, benzoic acid, butyric acid, chloroacetic acid, citric acid, crotonic acid, dimercaptosuccinic acid, formic acid, fumaric acid, gallic acid, glutaric acid, itaconic acid, lactic acid, malic acid, maleic acid, malonic acid, monanoic acid, methacrylic acid, naphtenic acid, oleic acid, oxalic acid, palmitic acid, paracetic acid, propionic acid, pimelic acid, salicylic acid, sebacic acid, succinic acid, stearic acid, sorbic acid, tartaric acid, thiomalic acid, uric acid, glyceric acid, xylonic acid, gluconic acid, neuraminic acid, ulosonic acid, ketodeoxyoctulosonic acid, glucuronic acid, galacturonic acid, iduronic acid, meso-galactaric acid, mucic acid, d-glucaric acid, saccharic acid, glycolic acid, mandelic acid, aspartic acid, glutamic acid, and mixtures thereof.

17. The pharmaceutical composition according to claim 15, wherein the inorganic acid is selected from hydrogen halides, halogen oxoacids, sulfuric acid, fluorosulfuric acid, nitric acid, phosphoric acid, fluoroantimonic acid, fluoroboric acid, hexafluorophosphoric acid, chromic acid, boric acid, and mixtures thereof, wherein the hydrogen halides are selected from hydrofluoric acid, hydrochloric acid, hydrobromic acid, and hydroiodic acid, and wherein the halogen oxoacids are selected from hypochlorous acid, chlorous acid, chloric acid, perchloric acid, hypobromous acid, bromous acid, bromic acid, perbromic acid, hypoiodous acid, iodous acid, iodic acid, and periodic acid.

18. The pharmaceutical composition according to claim 15, in the form of (i) a tablet or (ii) a capsule or (iii) a multilayer tablet, wherein (i), (ii) or (iii) comprise pellets, which pellets comprise dabigatran etexilate pellets or dabigatran etexilate mesylate pellets, together with proton pump inhibitor pellets and acid pellets.

19. The pharmaceutical composition according to claim 18, said dabigatran etexilate pellets or dabigatran etexilate mesylate pellets further comprising methacrylic acid-ethyl acrylate copolymer or polyvinyl alcohol or lactose monohydrate or sugar or polyvinylpyrrolidone or dibasic calcium phosphate or mixtures thereof.

20. The pharmaceutical composition according to claim 18, wherein said acid pellets comprise adipic acid or sorbic acid or succinic acid or glutaric acid or nitric acid and wherein the one or more pharmaceutically acceptable excipient is xanthan gum or isopropyl alcohol or sodium alginate or microcrystalline cellulose or mannitol or lactose or silicon dioxide or methacrylic acid-ethyl acrylate copolymer or polyvinyl alcohol or mixtures thereof.

21. The pharmaceutical composition according to claim 18, wherein said proton pump inhibitor pellets further comprise sugar pellet or mannitol or sodium starch glycolate or magnesium carbonate or povidone or sucrose or poloxamer or polyvinyl alcohol or methacrylic acid-ethyl acrylate copolymer or talc or triethyl citrate or simethicone emulsion or dibasic calcium phosphate or polyvinylpyrrolidone or polyvinyl acetate or mixtures thereof.

22. The pharmaceutical composition according to claim 18, wherein said proton pump inhibitor pellets further comprise enteric coating in an amount of 1% to 20% (w/w) of the total weight of the pellets.

23. The pharmaceutical composition according to claim 18, wherein said proton pump inhibitor pellets further comprise enteric coating in an amount of 2% to 20% (w/w) of the total weight of the pellets.

24. The pharmaceutical composition according to claim 18, wherein said pharmaceutical composition is in the form of tablet or capsule or multilayer tablet comprising the pellets, and wherein the pellets are bilayer or multilayer.

* * * * *